United States Patent
Kahya et al.

(10) Patent No.: US 10,716,533 B2
(45) Date of Patent: Jul. 21, 2020

(54) AUSCULTATION DATA ACQUISITION, COMMUNICATION AND EVALUATION SYSTEM INCORPORATING MOBILE FACILITIES

(71) Applicant: ELECTROSALUS BIYOMEDIKAL SAN. VE TIC. A.S., Istanbul (TR)

(72) Inventors: Zeynep Yasemin Kahya, Istanbul (TR); Ipek Sen, Istanbul (TR)

(73) Assignee: ELECTROSALUS BIYOMEDIKAL SAN. VE TIC. A. S., Istanbul (TR)

( * ) Notice: Subject to any disclaimer, the term of this patent is extended or adjusted under 35 U.S.C. 154(b) by 317 days.

(21) Appl. No.: 15/311,172

(22) PCT Filed: May 12, 2015

(86) PCT No.: PCT/TR2015/000199
§ 371 (c)(1),
(2) Date: Nov. 14, 2016

(87) PCT Pub. No.: WO2015/174944
PCT Pub. Date: Nov. 19, 2015

(65) Prior Publication Data
US 2017/0071565 A1 Mar. 16, 2017

(30) Foreign Application Priority Data
May 12, 2014 (EP) .................................... 14167878

(51) Int. Cl.
*A61B 7/04* (2006.01)
*G06F 19/00* (2018.01)
*G16H 40/63* (2018.01)

(52) U.S. Cl.
CPC ............ *A61B 7/04* (2013.01); *G06F 19/3418* (2013.01); *G16H 40/63* (2018.01)

(58) Field of Classification Search
CPC ....... A61B 7/04; A61B 5/7235; A61B 5/7239; A61B 5/7246; A61B 5/7253;
(Continued)

(56) References Cited

U.S. PATENT DOCUMENTS

| 5,218,969 A | 6/1993 | Bredesen et al. |
| 6,648,820 B1 * | 11/2003 | Sarel .................... A61B 5/0002 600/300 |

(Continued)

FOREIGN PATENT DOCUMENTS

| WO | WO2011049293 A1 | 4/2011 |
| WO | WO2013089072 A1 | 6/2013 |

OTHER PUBLICATIONS

O'Donnell and Kraman, Vesicular lung sound amplitude mapping by automated flow-gated phonopneumography, 1982, American Physiological Society, p. 603-609.*

(Continued)

*Primary Examiner* — Daniel L Cerioni
*Assistant Examiner* — Raymond P Dulman
(74) *Attorney, Agent, or Firm* — Bayramoglu Law Offices LLC

(57) ABSTRACT

A system having a chest piece for fitting to human skin, a receiver unit and a distant server; said chest piece encapsulates a sound transducer for acquiring raw sound data for being communicated as data signal; said receiver, in operation, is in communication with said chest piece; said receiver is a portable device having a display unit and data processing ability, and is further connectable to a local data network or global internet; said distant server comprises computer coded instructions which, in operation, processes said data signals, stores medical information and communicates said (Continued)

data signals and/or medical information with at least two recipients, the recipients are able to communicate information.

7 Claims, 13 Drawing Sheets

(58) Field of Classification Search
CPC ..... A61B 5/7257; A61B 5/726; A61B 5/7264; A61B 5/7267; A61B 5/7282; G06F 19/00
See application file for complete search history.

(56) References Cited

U.S. PATENT DOCUMENTS

| | | | |
|---|---|---|---|
| 10,029,056 B2* | 7/2018 | Reilly | A61B 5/7267 |
| 2006/0245597 A1* | 11/2006 | Guion-Johnson | A61B 7/04 |
| | | | 381/67 |
| 2008/0082017 A1* | 4/2008 | Savic | A61B 7/003 |
| | | | 600/529 |
| 2008/0146276 A1 | 6/2008 | Lee | |
| 2009/0234672 A1 | 9/2009 | Dicks et al. | |
| 2010/0305633 A1* | 12/2010 | Aziz | A61B 5/0205 |
| | | | 607/3 |
| 2011/0001605 A1* | 1/2011 | Kiani | G06F 19/3418 |
| | | | 340/5.6 |
| 2011/0087135 A1* | 4/2011 | Ferzli | A61B 7/04 |
| | | | 600/586 |
| 2011/0184250 A1* | 7/2011 | Schmidt | G06Q 10/00 |
| | | | 600/300 |
| 2011/0191343 A1* | 8/2011 | Heaton | G06F 19/00 |
| | | | 707/737 |
| 2012/0253849 A1 | 10/2012 | Parker et al. | |
| 2012/0289852 A1* | 11/2012 | Van Den Aardweg | |
| | | | A61B 5/085 |
| | | | 600/533 |
| 2013/0060110 A1* | 3/2013 | Lynn | A61B 7/003 |
| | | | 600/324 |
| 2013/0102908 A1* | 4/2013 | Ser | A61B 7/003 |
| | | | 600/484 |
| 2013/0150744 A1* | 6/2013 | Brattain | A61B 5/4848 |
| | | | 600/529 |
| 2013/0208970 A1* | 8/2013 | Fujisawa | A61B 6/032 |
| | | | 382/131 |
| 2013/0209068 A1* | 8/2013 | Lynn | G06F 19/321 |
| | | | 386/278 |
| 2014/0048072 A1* | 2/2014 | Angelico | A61M 16/0051 |
| | | | 128/204.23 |
| 2014/0107515 A1 | 4/2014 | Lee et al. | |
| 2014/0155774 A1* | 6/2014 | Sarrafzadeh | A61B 5/4818 |
| | | | 600/529 |
| 2014/0228657 A1* | 8/2014 | Palley | A61B 5/6823 |
| | | | 600/324 |
| 2014/0275852 A1* | 9/2014 | Hong | A61B 5/02427 |
| | | | 600/301 |
| 2015/0073306 A1* | 3/2015 | Abeyratne | A61B 7/003 |
| | | | 600/586 |
| 2015/0230751 A1 | 8/2015 | Yamanaka et al. | |
| 2015/0238270 A1* | 8/2015 | Raffy | A61B 34/10 |
| | | | 600/407 |
| 2015/0313535 A1* | 11/2015 | Alshaer | A61B 5/4812 |
| | | | 600/529 |
| 2016/0256073 A1* | 9/2016 | Grudin | A61B 5/087 |

OTHER PUBLICATIONS

Hans Pasterkamp et al, State of the Art Respiratory Sounds Advances Beyond the Stethoscope Introduction Sound at the Body Surface Stethoscopes Sensors for Lung Sound.
Recording Sound Transmission Models and Predictions Sound Transmission Measurements Effects of Pulmonary Pathology Respiratory Sounds Classification and Nome.
Am J Respir Crit Care Med, Jan. 1, 1997 (Jan. 1, 1997), pp. 974-987, XP055190271.
Retrieved from the Internet:URL:http://vvvvw.atsjournals.org/doi/pdf/10.1164/ajrccm. 156.3.9701115 [retrieved on May 20, 2015].

* cited by examiner (a)

(b)

AUSCULTATION DATA ACQUISITION, COMMUNICATION AND EVALUATION SYSTEM INCORPORATING MOBILE FACILITIES

TECHNICAL FIELD OF THE INVENTION

The present invention relates to an auscultation data acquisition, communication and evaluation system incorporating mobile facilities, comprising a chest piece for acquiring auscultation data and communicating said data in the form of a signal, a receiver unit and a distant server for communicating with said receiver unit and at least a further recipient relevantly selected from a list entailing suitable devices appropriated for use by healthcare personnel, medical facilities and users such that data and information are shared selectively in accordance with said recipients.

BACKGROUND OF THE INVENTION

Electronic auscultation devices are gaining increasing popularity in medical industry. Some examples for them combine a stethoscope with an LCD screen and control buttons which can also record and communicate sounds to other devices for later evaluation by health professionals. Audio frequency responses of such devices are similar with acoustic stethoscopes. Their main advantage in comparison with acoustic stethoscopes is amplification ability for easier hearing of said sounds.

Intelligent stethoscopes are not yet common, but considering a few patent applications on this subject, it is possible to expect such devices to be available in medical market.

US 2008 146 276 A1 discloses a device functioning in combination with a telephone, which compares digitized auscultation data with standardized disease sounds on a data storage unit integrated with said telephone, and a disease name appears on the telephone screen. As yet, need for data storage units with sufficient capacities for storing great amounts of data, and requirement of powerful processors for performing sophisticated calculations and algorithms for probabilistic diagnosis limits the use of said idea with every smartphone. Furthermore, the device disclosed in said application transmits only disease names to health professionals, which limits the health professional from using his/her own technical knowledge for reaching a decision by evaluations based on auscultation data.

International patent application WO 2011 049 293 discloses a device combining a stethoscope head with a mobile telephone. The device acquires auscultation sound via a microphone head, and a disease name appears on the telephone screen. Said device employs a temperature sensor which can serve for thermal checking whether the device is in proper contact with a subject's skin, yet such sensor which only aims to detect temperature is not suitable to distinguish whether said device is in contact with the proper body part or zone on a subject's skin to obtain meaningful auscultation data.

It is of vital importance to check whether auscultation data are collected from a proper zone on a subject's skin, and if the sound acquisition device is placed properly such that said meaningful auscultation data are not overridden by ambient noise. Furthermore, auscultation sounds have zone-specific characteristics both in healthy and pathological conditions, which fact necessitates the obligation to evaluate each collected sound data with regard to a corresponding database for each auscultation zone. In prior art, although auscultation sounds are collected with regard to zones of auscultation, auscultation sounds are compared with a single database without regard to distinctions between zones.

One of the most important factors in diagnostic classification problems in terms of reliability is having a sufficiently large database in conjunction with employing a sufficiently powerful processor for rapidly obtaining a general and acceptable result from a sophisticated algorithm. When processing of acquired auscultation data to propose a probabilistic diagnosis is made on a telephone device, the reliability of its results is restricted due to limitations on database size and algorithm sophistication since a phone processor has limited storing and processing capability.

A further important factor is taking into account the information about disease-specific auscultation sounds (e.g. crackles and wheezes) because the presence and characteristics of adventitious sounds are very important in determining the presence, type and severity of an underlying pathology. Although the systems and methods of prior art detect adventitious sounds such as crackles and wheezes, utilization of adventitious sounds in various phases of a respiration cycle in an algorithm which provides a probabilistic suggestion about medical state of a subject is not available in prior art.

U.S. Pat. No. 6,648,820 B1 discloses a medical condition sensing system including a multiplicity of computers connected via a network, yet the vision related to said document is limited to acquisition and comparison of variable data obtained from a single patient at different instances. Said system and related method leads to designate initial data from patient as a baseline, and generates alerts in case of significant variations from the initial data. Evolution of initially present databases related to various health conditions, or creating new databases related to diseases which are initially absent in database collections are unachievable and underivable from such system.

US 2013/0102908 A1 discloses an air conduction sensor and a system and a method for monitoring health condition, U.S. Pat. No. 5,218,969 A discloses an intelligent stethoscope for automatically diagnosing abnormalities; and US 2014/0107515 A1 discloses a telemedical stethoscope which automatically diagnoses diseases, and records and stores data. None of these documents mention nor lead to evolution of initially present databases related to various health conditions, or creating new databases related to diseases which are initially absent in database collections.

U.S. Pat. No. 5,218,969 discloses an intelligent stethoscope for automatically diagnosing abnormalities based on body sounds. Yet, said stethoscope lacks learning abilities since it can't enable the databases loaded thereon to evolve and nor create new databases related to diseases which are initially absent in its database collections. Furthermore, even though said document describes a method to obtain some diagnosis related to heart sounds; the chaotic nature of lung sounds renders said stethoscope inadequate for thorough and multidimensional handling of sound data for suggesting a probabilistic diagnosis.

Scientific research articles are available about computational analyses of auscultation sounds. Said articles generally discuss about acquisition of auscultation data, analog preprocessing i.e. filtration and amplification of said data, analog-to-digital conversion and transferring thereof to computers. Then, said data is subjected to analyses of spectral and temporal signal characteristics, detection and/or classification in terms of adventitious sounds (e.g. crackle and wheeze detection and/or classification), and classification in terms of conditions (e.g. healthy and pathological classification). Yet none of the classification methodologies in the literature uses a sophisticated combination of (i) information about adventitious sounds, (ii) information about general spectral, temporal and spatio-temporal sound characteristics, (iii) distinct information of respiration phases in a full respiration cycle (e.g. early, mid and late phases for both inspiration and expiration in a full respiration cycle), to propose a probabilistic diagnosis about medical state of a subject.

OBJECTS OF THE INVENTION

Primary object of the present invention is to provide a data acquisition, communication and evaluation system which overcomes abovementioned shortcomings of the prior art.

Another object of the present invention is to provide a data acquisition, communication and evaluation system which employs intelligent algorithms for providing health professionals and medical facilities (i.e. any location at which medicine is practiced regularly; for example, all health care institutions such as hospitals, health care centers, medical laboratories, research centers, etc.) with probabilistic evaluations of auscultation data.

Another object of the present invention is to provide a data acquisition, communication and evaluation system which enables initially present databases related to various health conditions to evolve, and/or creates new databases related to diseases which are initially absent in database collections in said system.

Additionally an object of the present invention is to provide a data acquisition, communication and evaluation system which uses sound data both for computational and aural evaluation of auscultation data.

Still further an object of the present invention is to provide data acquisition, communication and evaluation system which provides different levels of information obtained from auscultation data, the levels of which are suitable and meaningful for either medical facilities or healthcare personnel or users without medical training.

Yet another object of the present invention is to provide a data acquisition, communication and evaluation system, where auscultation data and any computations obtained from said data are simultaneously or subsequently available also to or from a location distant from the auscultation site.

SUMMARY OF THE INVENTION

A data acquisition, communication and evaluation system having a chest piece for fitting to human skin, a receiver unit and a distant server; wherein said chest piece encapsulates a sound transducer for acquiring raw sound data for being communicated in the form of a data signal; said receiver, in operation, is in communication with said chest piece; said receiver is a portable device having a display unit and data processing ability, and is further connectable to a local data network or global internet via wired or wireless communication interface; said distant server comprises computer coded instructions which, in operation, processes said data signals, stores medical information in association with said data signals and communicates said data signals and/or medical information with at least two recipients, wherein said at least two recipients are able to receive and send said data signals and/or said medical information, and wherein said at least two recipients are selected from the list consisting of devices held by healthcare personnel, medical facilities and users, said data signals and/or medical information are selective based on the selected recipient; the system, in operation, updates a computer-coded classifier as new data add to said database.

BRIEF DESCRIPTION OF THE FIGURES

The figures whose brief explanations are herewith provided are solely intended for providing a better understanding of the present invention and are as such not intended to define the scope of protection or the context in which said scope is to be interpreted in the absence of the description.

DETAILED DESCRIPTION OF THE INVENTION

Referring now to the figures outlined above, the present invention proposes a data acquisition, communication and evaluation system FIG. 1 having a chest piece 100, a receiver unit 200 and a distant server 300; which system overcomes abovementioned shortcomings of the prior art as described below in detail.

Figure 1:
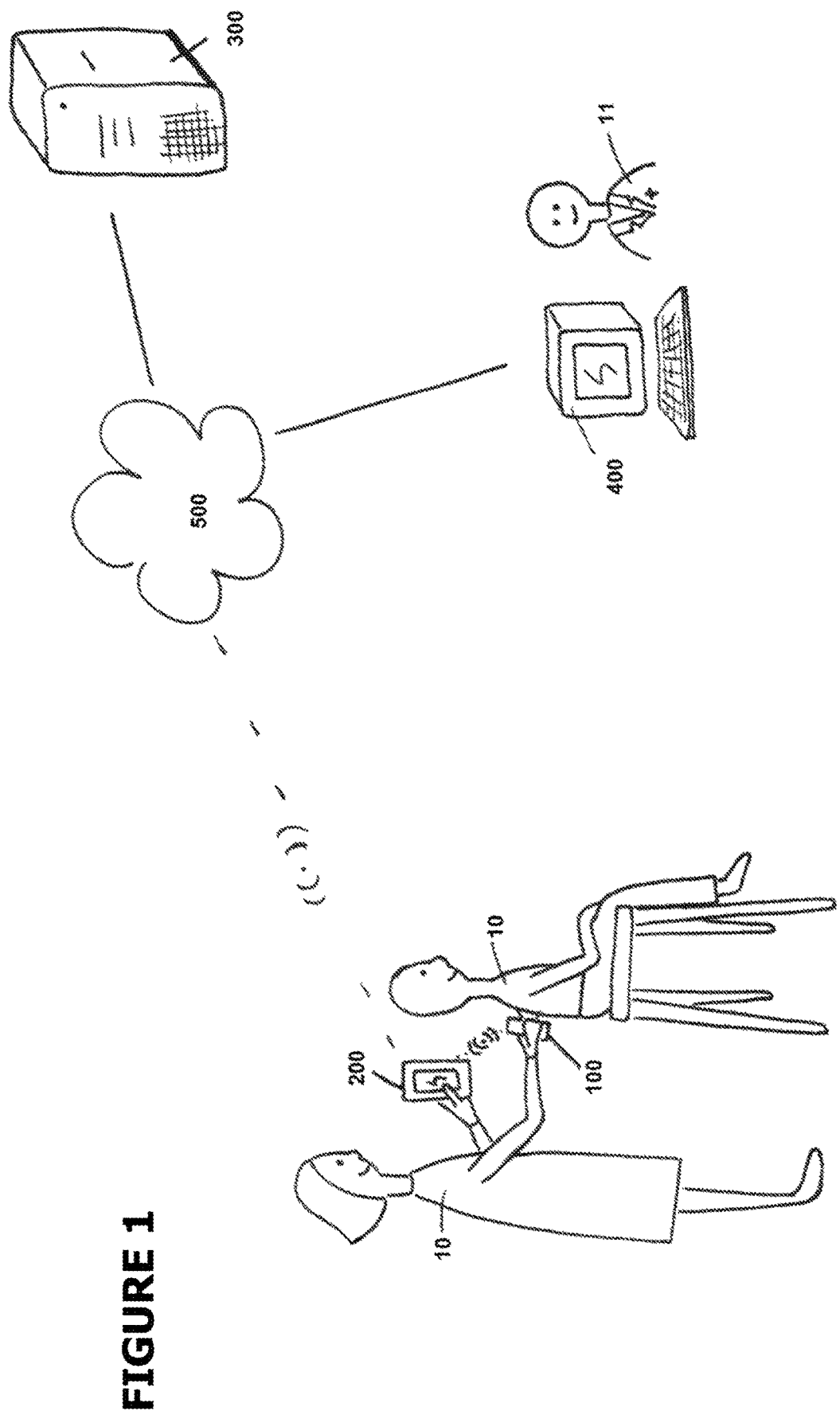
FIG. 1 represents a simplified pictorial diagram illustrating the operation of the data acquisition, evaluation and communication system according to the present invention.
Figure 2:
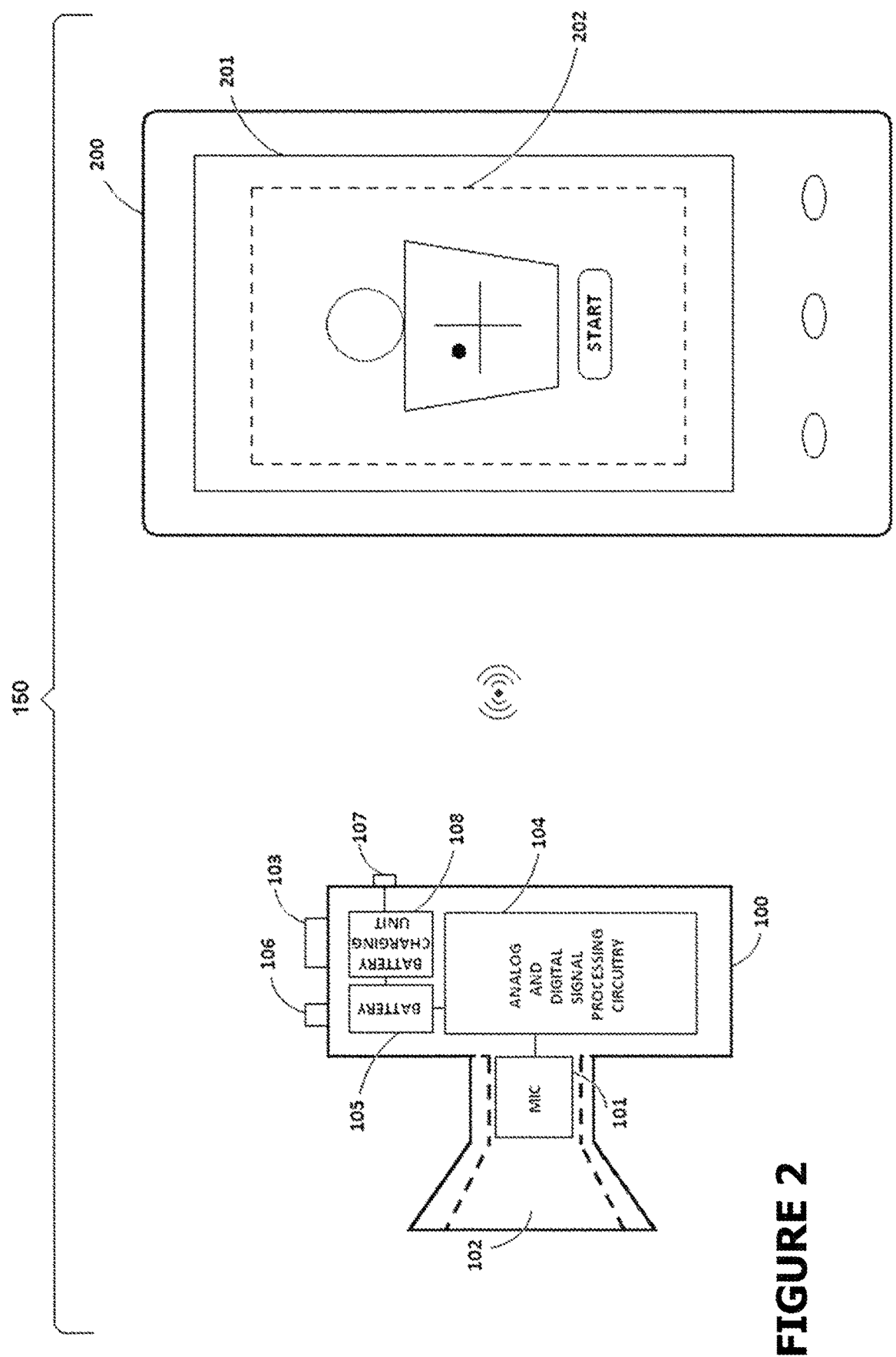
FIG. 2 schematically represents the chest piece and the receiver unit, both forming part of the system of FIG. 1 according to the present invention.

With reference to FIGS. 1 and 2, said system includes a data acquisition device 150 which is an auscultation device with data communication abilities. Said data acquisition device comprises a chest piece 100 and a receiver unit 200. Said chest piece 100 encapsulates a sound transducer 101 for acquiring raw sound data for being communicated in the form of a data signal, wherein said sound transducer 101 is any kind of transducer which transduces (converts) vibratory mechanical oscillation (e.g., acoustic motion of a membrane) to an electrical signal (e.g., accelerometers, deformation piezoelectric transducers, microphones).

Said system further comprises computer(s) 400 preferably placed in (a) medical facility(ies), and said system further comprises a main (distant) server 300. Said computers 400 are used for monitoring the data used in the system, for monitoring processed outcomes of said data, and for adding suitable information associated with said data to the system e.g. commentary information. Said server 300 is for processing and storing data and arranging proper operation of said system with selective authorization.

With reference to FIGS. 1 and 2, said chest piece 100 is an air coupling non-metallic chest piece for comfortably fitting to human skin, said chest piece 100 encapsulates a microphone 101 for acquiring raw sound data for being communicated in form of a data signal. Said chest piece 100 which is an air coupling unit can preferably provide a soft and non-cold touch to the skin by employing non-metallic material (e.g. polymers) for its parts contacting patient's skin, and provides preferably an ergonomic, comfortable grasp for user's hand. It preferably has a design for leaving an air coupling cavity 102 inside the chest piece 100 for proper operation of the air coupled microphone 101, while providing means for an air-tight contact of the chest piece 100 with patient's skin, thus preventing external noise.

Said receiver 200 is in communication with said chest piece 100, said receiver 200 having a display unit 201, and is a portable device with computing abilities, which can connect to a local data network or global internet 500 via wired or wireless communication interface. A smart phone or a tablet computer or any such mobile unit can be employed as said receiver unit 200.

Figure 13:
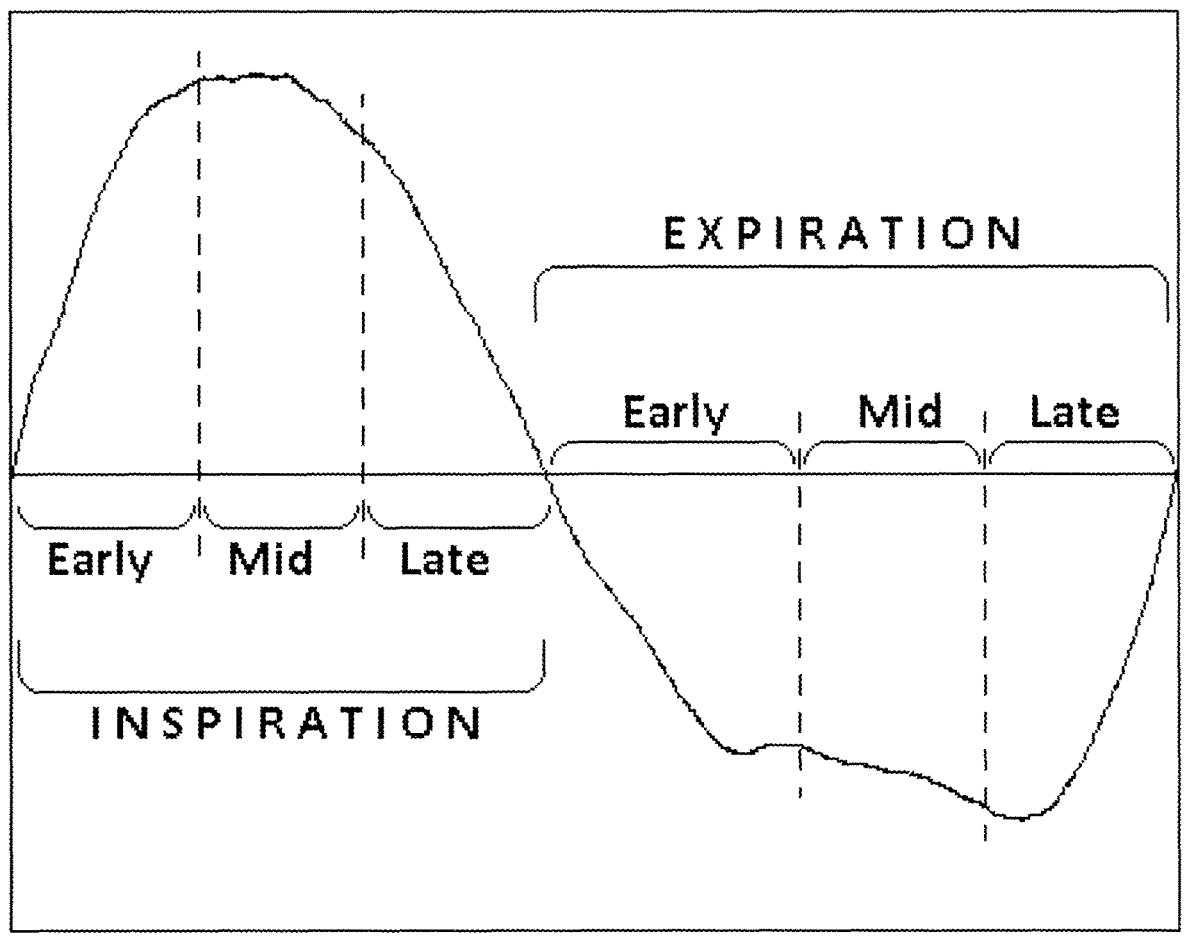
FIG. 13 shows a representative plot of a form of flow signal estimated from sound data, which is marked with inspiration and expiration phases and with early, mid and late sub-phases predicted by the flow estimation algorithm forming part of the evaluations of FIG. 6, using a system according to the present invention.

Said signal is a sound signal which can be used to estimate a form of air flow signal (see FIG. 13) using mathematical algorithms e.g. a time-varying parametric model for predicting inspiration and expiration phases within a flow cycle such that sub-phases of inspiration and sub-phases of expiration can be predicted. Said flow cycle is divided into sub-phases comprising early inspiration, mid inspiration, late inspiration, early expiration, mid expiration and late expiration. Thus, said system, in operation, estimates an air flow signal from said data signal using mathematical algorithms, predicts inspiration and expiration phases having sub-phases, within a flow cycle, and predicts sub-phases of inspiration and sub-phases of expiration (see FIG. 13).

The system according to the present invention, in operation, detects and computes
spectral and temporal characteristics of crackles, comprising timing, frequency content, types in terms of fine, medium and coarse ranges, and counts, and
spectral and temporal characteristics of wheezes, comprising timing, at least one peak frequency component, and a percentage of duration within said sub-phases of inspiration and expiration, within inspiration and expiration, within flow cycle, and over total auscultation period.

In a further preferred embodiment according to the present invention, said system, in operation, displays a plot of said signal in time domain with zooming and sliding capabilities, and said plot shows said sub-phases (see 2100 in FIG. 12) and adventitious sounds comprising said detected crackles and wheezes.

The system according to the present invention, in operation, generates and displays a frequency-domain representation with regard to each said zone and each said sub-phase, from which said system calculates and displays various parameters related to auscultation and makes comparisons of said parameters against related parameters obtained from healthy reference data, and displays (see 2200 in FIG. 12) results of said comparisons.

Figure 12:
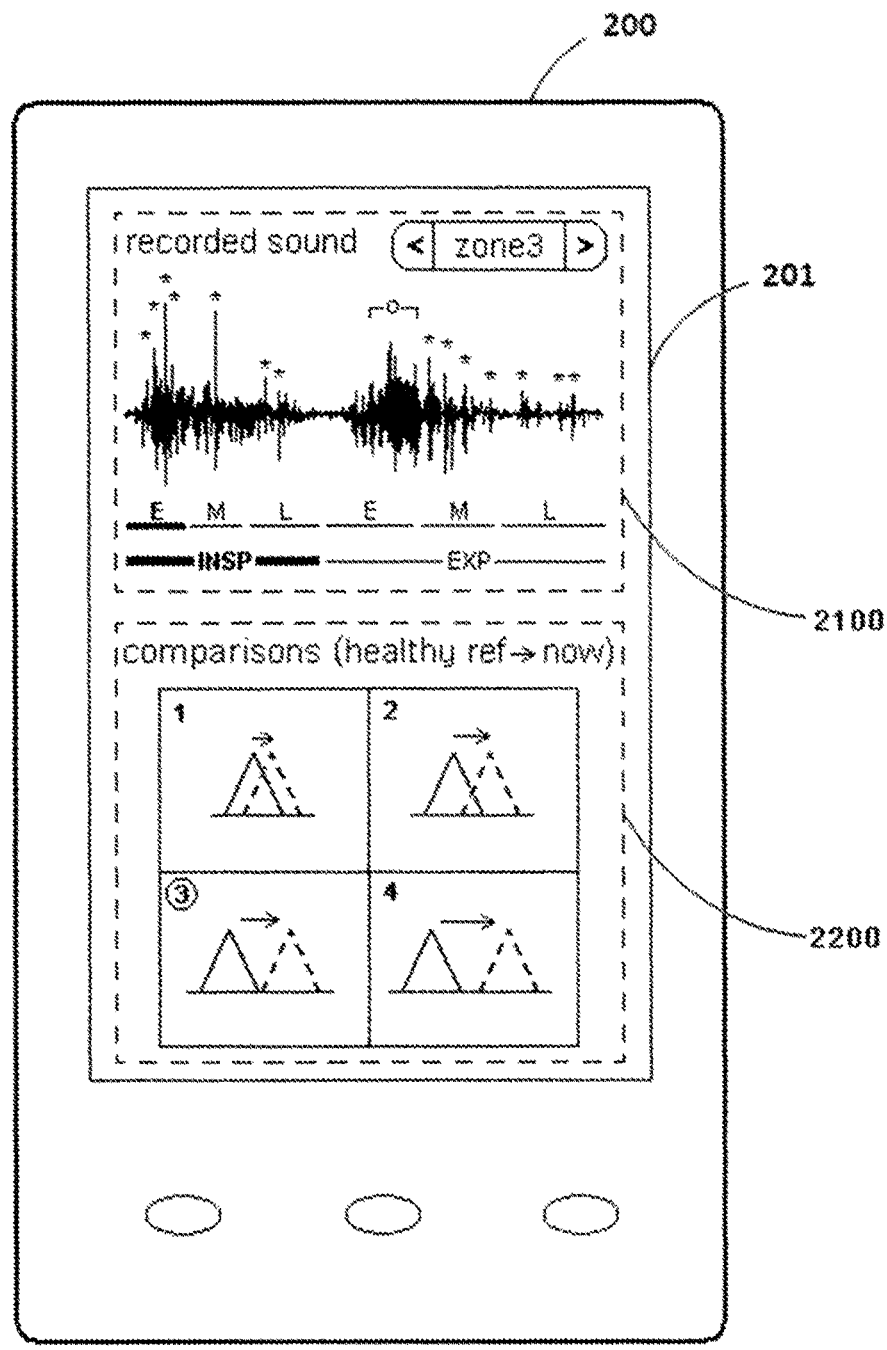
FIG. 12 shows a representative illustration of a receiver unit of the system according to the present invention with exemplary graphical outputs displayed on its screen.

In operation, said system displays a plot of said signal can preferably be displayed in time domain with zooming and sliding capabilities, for showing crackles, wheezes and said sub-phases (see 2100 in FIG. 12). A frequency-domain representation is obtained and displayed with regard to each zone and each sub-phase, from which various parameters related to auscultation are calculated, displayed and compared against those obtained from healthy reference data, the results of which are also displayed (see 2200 in FIG. 12) in various formats.

The data acquisition, communication and evaluation system according to the present invention is provided with separate databases, each of said databases is related with a different respective pre-determined zone on human torso.

Said system further comprises a plurality of pre-defined data acquisition channels and/or data acquisition locations for evaluating data from each said zone and said system, in operation, generates directives for a user to place said chest piece at said pre-determined zones in accordance with a pre-determined sequence.

Figure 8:
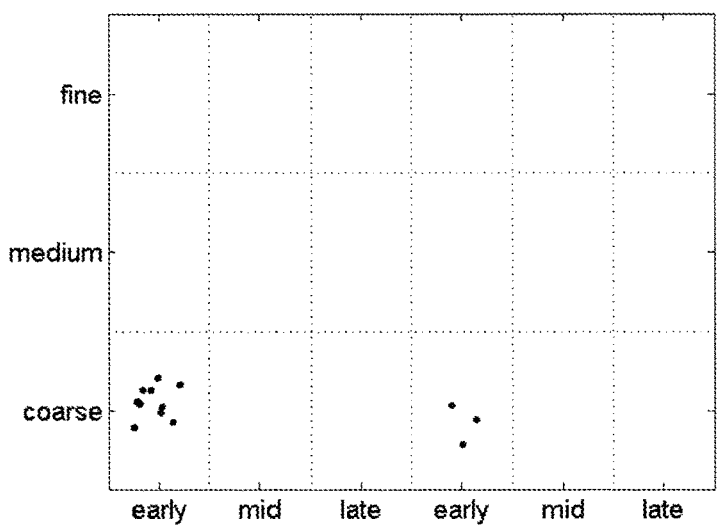
FIG. 8 shows representative illustrations for one type of graphical outputs provided by the system according to the present invention, for three different subjects, which displays detected crackles in a time-frequency representation where time is expressed in terms of sub-phases of flow cycle and frequency is expressed in terms of crackle types.
Figure 8:
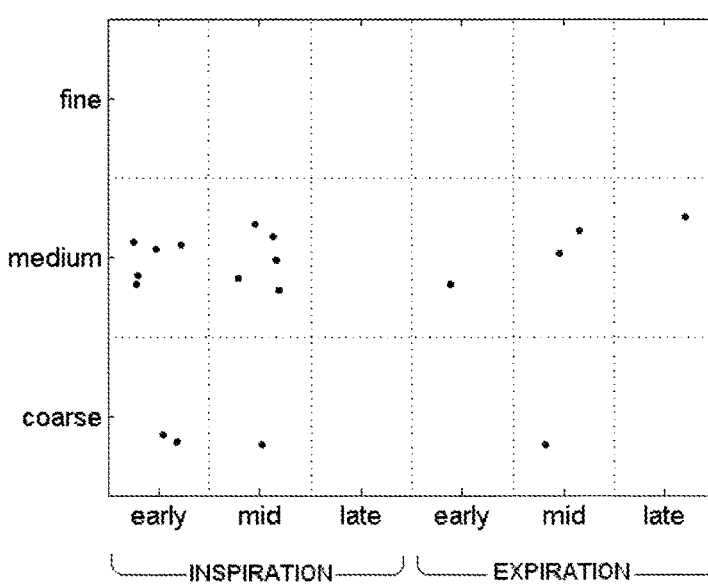
Figure 8:
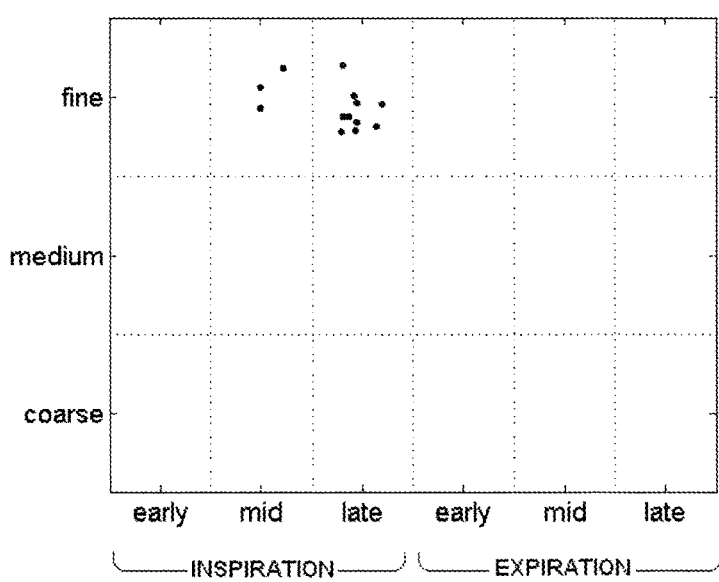
Figure 9:
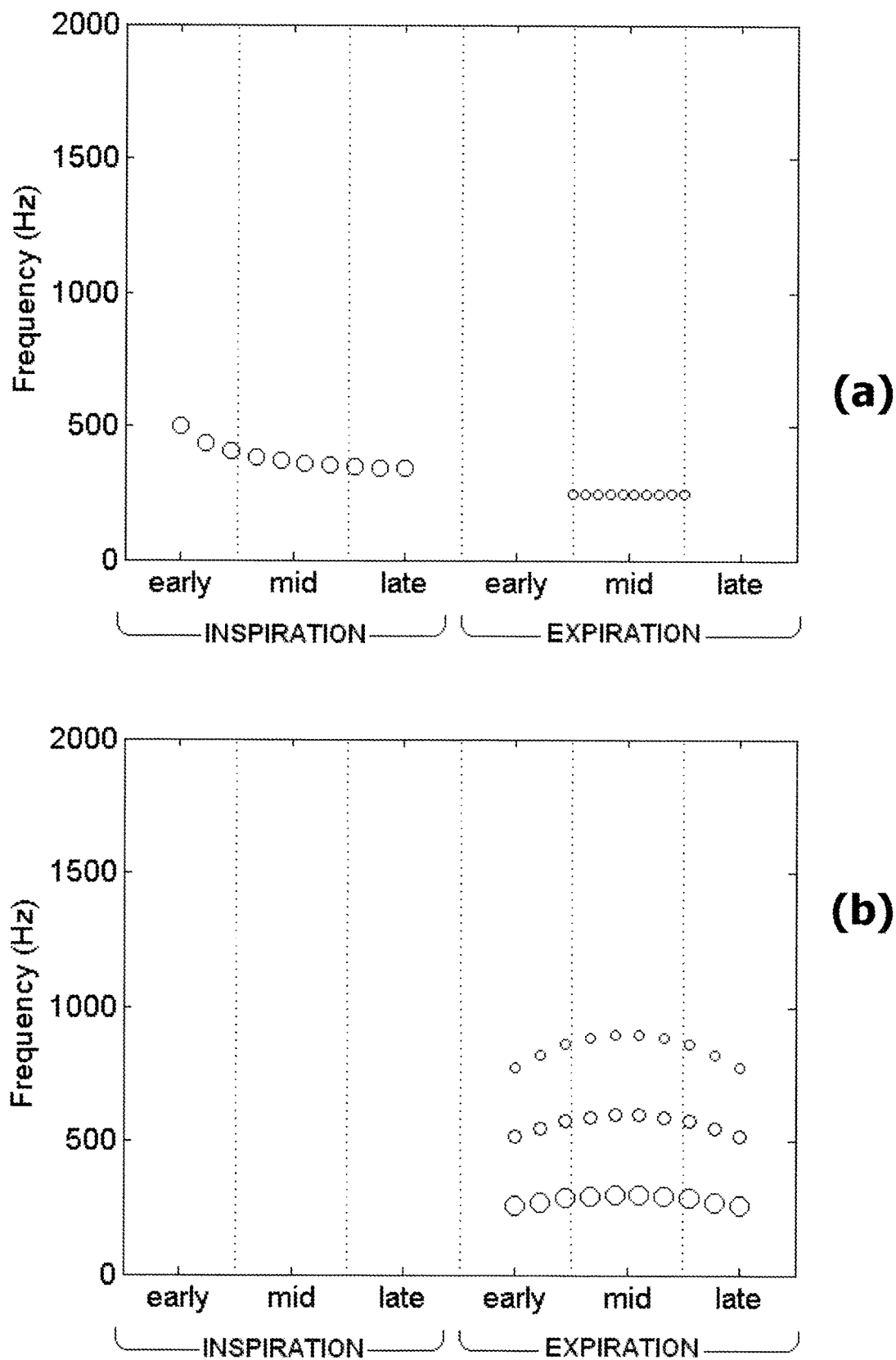
FIG. 9 shows representative illustrations for another type of graphical outputs provided by the system according to the present invention, for two different subjects, which displays detected wheezes in a time-frequency representation where time is expressed in terms of sub-phases of flow cycle and frequency is a continuous axis.

Spectral and temporal characteristics of said crackles having crackle frequencies in terms of fine, medium and coarse ranges, further having counts, and further having types are detected, computed and displayed in a time-frequency representation (see FIG. 8), where time is expressed in terms of said sub-phases starting with early inspiration and ending with late expiration, and frequency is expressed in terms of fine, medium and coarse crackle frequency ranges. Spectral and temporal characteristics of said wheezes, comprising timing, at least one peak frequency component and a percentage of duration within said sub-phases, flow cycle, and a total auscultation period are detected, computed and displayed in a time-frequency representation (see FIG. 9), where time is expressed in said sub-phases starting with early inspiration and ending with late expiration and where frequency is a continuous axis. Said count of said types of crackles and wheezes are preferably mapped with regard to said zones for displaying with color codes and shape codes in regard with said zones (see FIG. 10 and FIG. 11) on a display.

Figure 6:
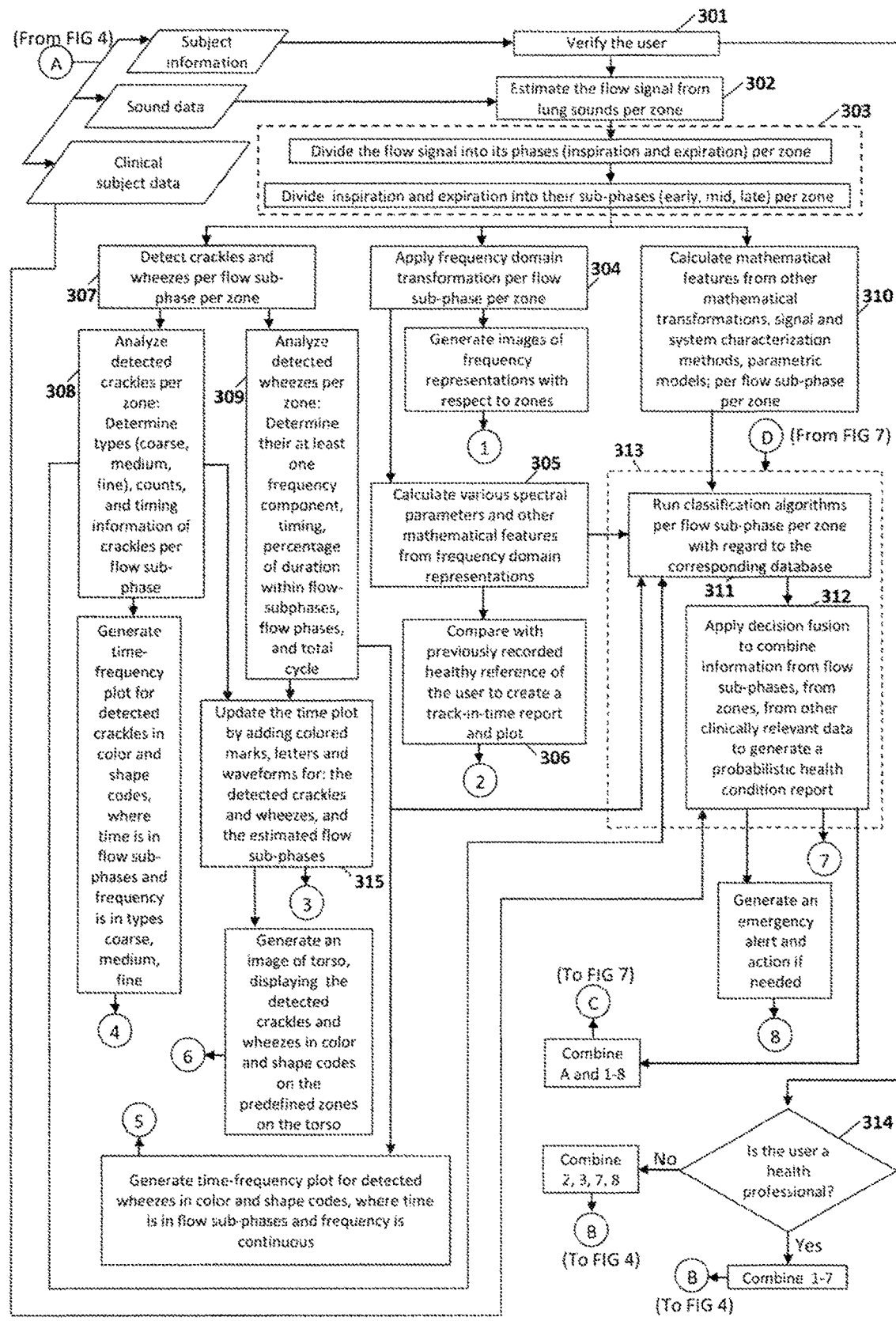
FIG. 6 shows a simplified flowchart illustrating the evaluations performed on the distant server forming part of the system of FIG. 1 according to the present invention.

The system according to the present invention further comprises a computer-coded classifier 313 in FIG. 6 which, in operation, utilizes information from said frequency-domain representations (see 305 in FIG. 6), and said time-frequency representations (see FIG. 8, FIG. 9, and 308 and 309 in FIG. 6) for each zone and sub-phase, together with mathematical transforms, signal and system characterization methods, parametric models (see 310 in FIG. 6), and said computer-coded classifier 313, in operation, combines data and calculations for each zone and sub-phase, and generates a probabilistic health condition report with regard to said database.

Figure 7:
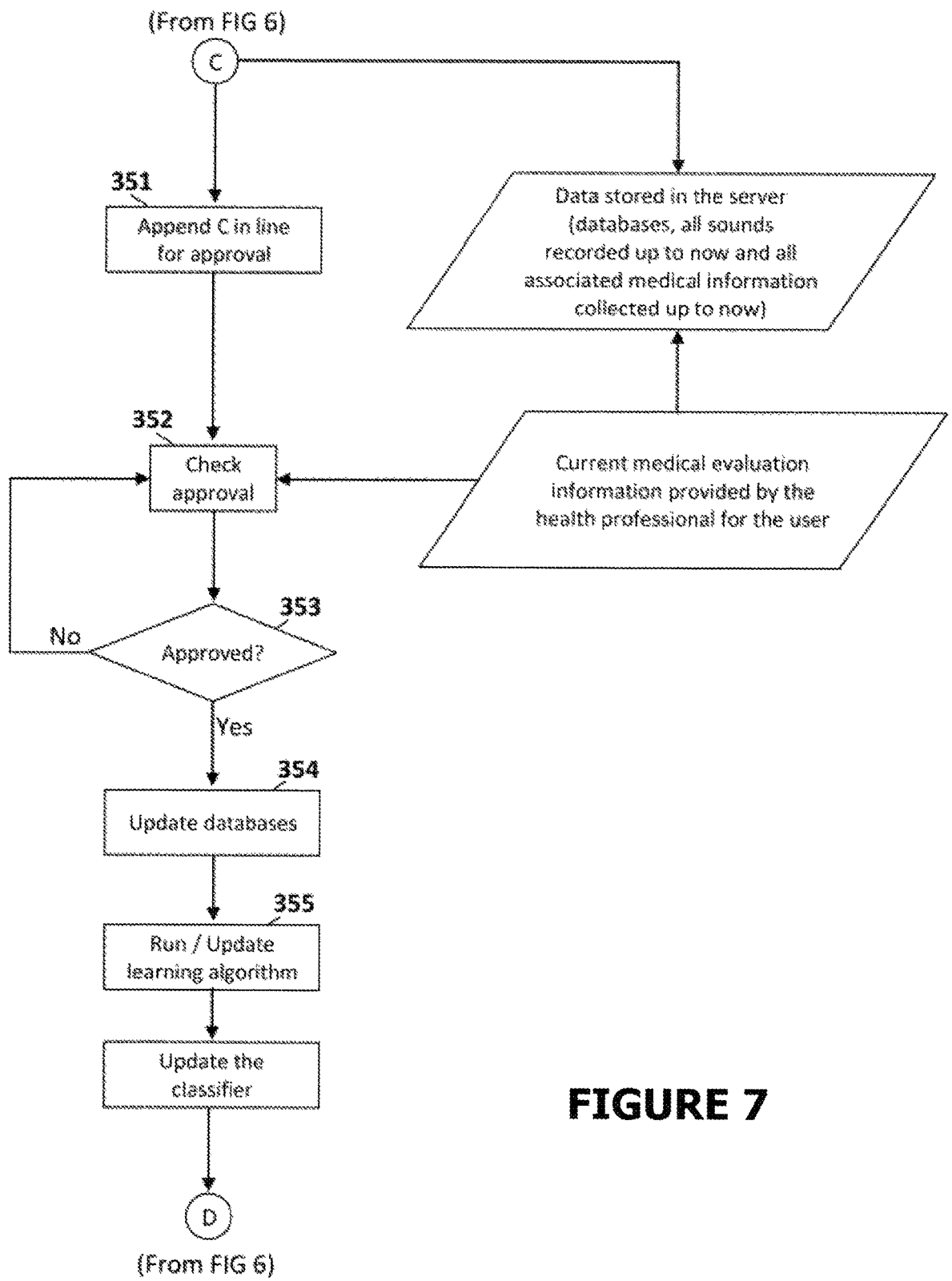
FIG. 7 shows a simplified flowchart illustrating the update mechanism operated by a distant server to update the databases, the learning algorithm, and the classifier of the system according to the present invention.

The system according to the present invention, in operation, updates said computer-coded classifier 313 as new data add to said database (see 354 in FIG. 7). Thus, by employing intelligent algorithms for updating said computer-coded classifier 313, said system provides probabilistic evaluations of auscultation data. By means of said updating ability, a data acquisition, communication and evaluation system which enables initially present databases related to various health conditions to evolve, and/or creates new databases related to diseases which are initially absent in database collections in said system, is provided.

With reference to FIGS. 1 and 2, the system further includes a distant server 300. Said distant server 300 is a component for evaluation and storage of data and communication received from other components of the system i.e. the data acquisition device 150 and computer(s) 400. Said distant server 300 comprises computer coded instructions which, in operation, processes said data signals, stores medical information in association with said data signals and communicates said data signals and/or medical information with at least two recipients, wherein said at least two recipients are selected from the list consisting of devices 200 and 400 held by healthcare personnel 11, medical facilities and users 10. Said recipients are able to receive and send said data signals and/or said medical information. The distant server 300 is preferably the central component responsible for general coordination of the system. The distant server 300 is for processing said data, for storing medical information based on and associated with said data and for communicating said data and information with at least two further recipients. Said data signals and/or medical information are selective based on the selected recipient. The users can also be defined as normal users 10 without medical training and which perform auscultation; healthcare personnel 11 who uses the data acquisition device and associated computers in medical facilities, including nurses, physicians and other healthcare personnel; and other personnel responsible for proper operation of the system with or without medical training, who work in a medical facility, who are responsible for the coordination of health services associated with the system of the present invention, and who are assigned users of computers which are part of said system. It is envisioned that as processors used in mobile devices are more developed and have stronger capabilities, the facilities of the system may be contained in an application program.

In a further preferred embodiment according to the present invention, information including data recorded from a subject and associated medical information which is selected from the list consisting of subject information, clinical subject data, algorithmic evaluation and outcomes from said system, and medical evaluation information provided by a healthcare personnel, are selectively accessible for users, such that respective data can be accessed by non-health-professional users 10 e.g. a patient, health professionals 11 making the auscultation or checking the data in a distant place, and employees of a medical facility providing access to said data through a server or computer which is a part of the system according to the present invention.

Thus, with the system according to the present invention, auscultation data and any computations obtained from the data are simultaneously or subsequently available also from a location distant from the auscultation site.

In a further preferred embodiment according to the present invention, the communication and evaluation system tracks in time said probabilistic health condition and reports any changes in said probabilistic health condition or said parameters selectively for users, such that respective data can be accessed by health professionals, healthcare personnel and non-healthcare personnel users.

Figure 5:
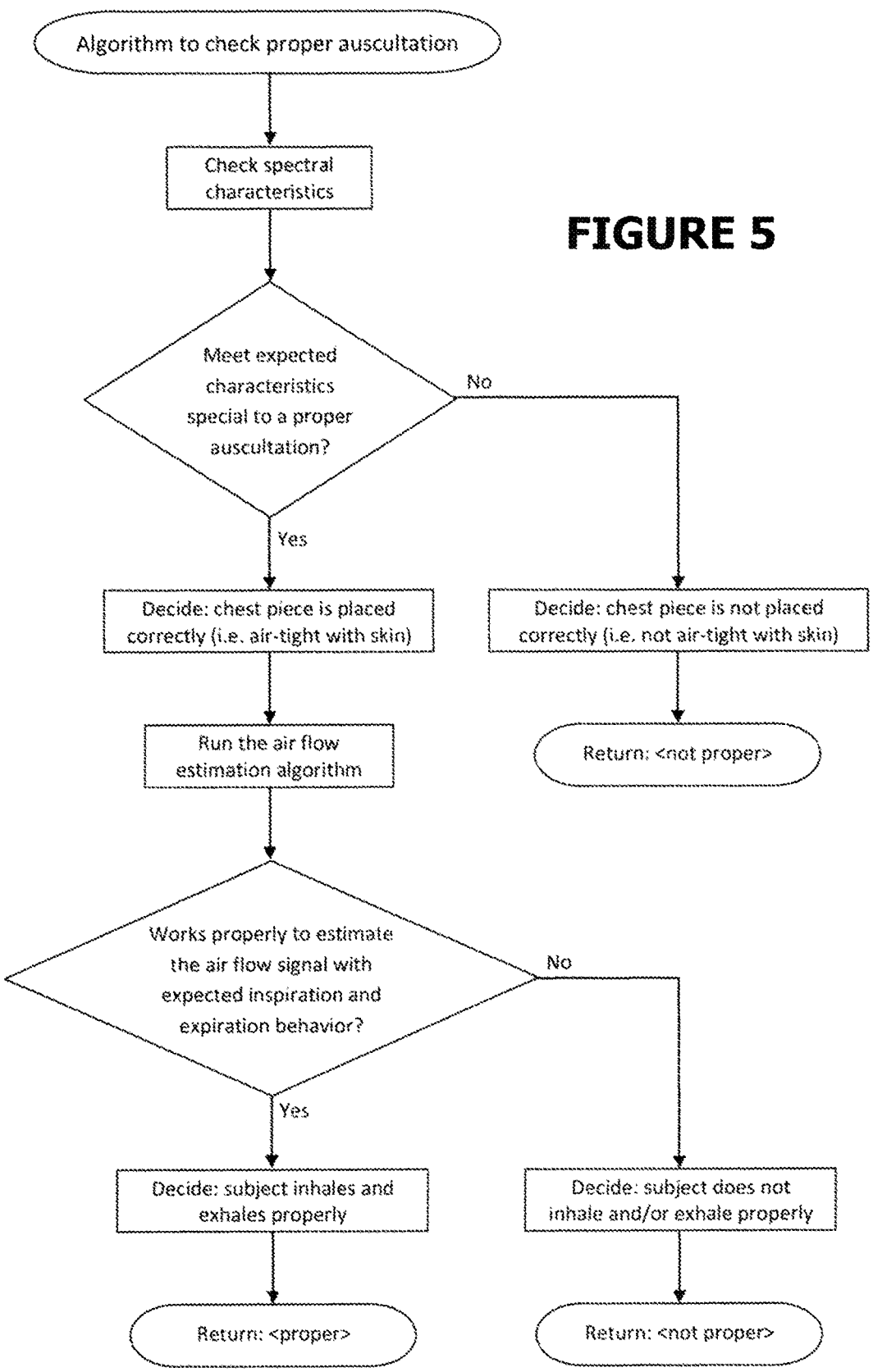
FIG. 5 shows a simplified flowchart illustrating an exemplary operational flow of an algorithm to check proper auscultation, which is part of the application program of FIG. 4, according to the present invention.

In a preferred embodiment according to the present invention, said system, in operation, checks for proper auscultation (see FIG. 5) by checking (i) whether said chest piece is placed correctly (e.g. by checking whether auscultation data meets the expected spectral characteristics special to a proper auscultation), and (ii) whether a subject inspires and expires properly such that sufficient air volumes for collecting data is inhaled and exhaled (e.g. by checking whether the air flow estimation algorithm works properly to estimate the air flow signal with expected inspiration and expiration behavior).

In a further preferred embodiment according to the present invention, said system, in operation, filters said signals according to a pre-defined frequency response shape including conventional bell and diaphragm modes, for listening by a user.

Figure 3:
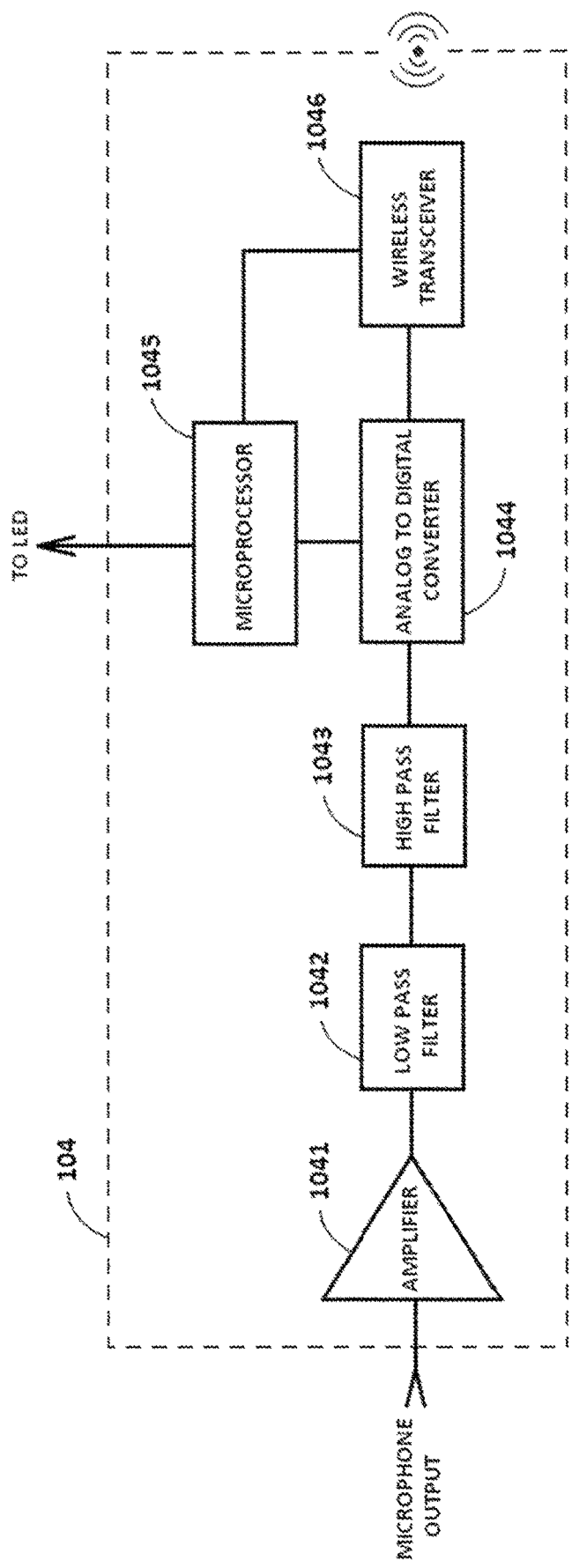
FIG. 3 shows a simplified functional block diagram of the general functionality of the analog and digital signal processing circuitry of the chest piece forming part of the system of FIG. 1 according to the present invention.

Referring to the FIGS. 2 and 3, the chest piece 100 is preferably provided with one or more control switches 103 for enabling single-hand operation to turn said chest piece 100 on and off while holding it. The chest piece 100 comprises (without limitation) following elements: an analog and digital signal processing circuitry 104 having amplifier(s) 1041, filter(s) 1042 and 1043, analog-to-digital converter(s) 1044, processor(s) 1045, a wireless transceiver 1046; and said chest piece 100 may further comprise a battery 105, control switches 103, status displaying LEDs 106, and a slot 107 for battery charging unit 108 plug.

Said wireless transceiver 1046 can work in any possible version of the Bluetooth protocol, or in any one of other wireless communication protocols. Said battery 105 can be rechargeable through the charging slot 107, and during the charging, the operation of the device can be limited to prevent any risks with the electrical current. The status of the battery and the charging process can be visualized through multiple LEDs with different colors, or with a single multi-colored LED 106. The status of the Bluetooth connection between said chest piece and the receiver unit can also be visualized through multiple LEDs with different colors, or with a single multi-colored LED 106, or with one single-colored LED which is 'off' when disconnected, 'on' when connected, and 'blinking' when trying to establish a connection. The chest piece 100 can be provided with a control switch 103 to turn on/off said piece 100 to save power during the time the device is unused. Said control switch 103 can be a push-button, a slide, a toggle, a rocker, or any other suitable switch type. The chest piece 100 can also be designed to go into a sleep mode if the receiver unit 200 does not send any command during a predefined interval of time.

In an alternative embodiment, the chest piece 100 can also be connected to the receiver unit 200 with a wired connection. In such case, one or more components in the analog signal processing circuitry 104 of the chest piece 100 would not be necessary, but instead for example a standard 3.5 mm or other audio output port can replace said unnecessary components. In yet another embodiment, output signal of the chest piece 100 can be carried directly with a cable which is not necessarily in accordance with any audio standard, to an external analog/digital circuitry in connection with the receiver unit 200 through a brand-specific conventional connection e.g. micro USB or lightning.

Alternative embodiments can employ receiver units 200 other than smart phones or tablet computers, where such receiver unit 200 includes a wireless radio transceiver (e.g. Bluetooth, Zigbee) for communicating with said chest piece 100, processor(s), a memory, a display screen 201 (preferably a touch screen), switch(es), a battery, a battery-charging slot, an application program 202, and wired (e.g. PLC, DSL, fiber) and wireless (e.g. 2G/3G cellular, GPRS, Wi-Fi, Wimax, LTE) communication capabilities for communicating with at least two further recipients other than said chest piece 100, including said distant server 300. If the chest piece 100 of such embodiment is cable-connected to an external analog/digital circuitry 104, then the connection between the analog/digital circuitry 104 to the receiver unit 200 can be made through a design-specific non-conventional connection type. Alternatively, such external analog/digital circuitry 104 can also be integrated into the receiver unit 200, enabling the chest piece to be cable-connected directly to said receiver unit 200.

Referring to the FIGS. 1 and 2, in an alternative embodiment according to the present invention, the chest piece 100 and the receiver unit 200 are combined in one casing, then the combined chest piece-receiver unit can be designed to connect directly to a local data network or global internet 500 via wired or wireless communication interface to communicate with other components of the system. Alternatively, another embodiment according to the present invention combines the chest piece 100 and the receiver unit 200 while still using a smart phone or tablet computer as receiver unit 200, wherein the chest piece 100 is installable at the back of said receiver unit 200 as conventional phone/tablet dock-cases do. In such case, auscultation is to be performed by contacting a side of the device with the microphone 101 onto chest wall of a subject being auscultated, while the display screen 201 of the device facing towards the user conducting the auscultation. Therefore, such embodiment would especially offer a useful design for accompanied-auscultations, e.g., those performed by an accompanying family member or by healthcare personnel.

Referring to the FIGS. 1, 2, 4, 5, 6 and 7, an example for a typical operation of the preferred embodiment of the data acquisition (auscultation) device by the normal user is described as follows. The user starts (see 2021 in FIG. 4) an application program 202 on the receiver unit 200, and follows several graphical, written and vocal directives generated by said application program to ensure a proper data acquisition session. If it is a first-time use (see 2022), said directives may first lead the user to enter his/her name, surname, age, gender, and other useful information for identification, thus for creating a user account (see 2023). Multiple users can be defined in such application program, e.g., members of a family can create accounts for themselves using the same device. If it is not a first-time use for a specific user, the user enters the application program 202 through his/her own account (see 2024), and several directives (see 2026) lead the user to turn on the chest piece 100 e.g. using a switch 103 (if it is 'off' at that instant), to enable a wireless connection e.g. a Bluetooth connection on receiver unit's side (if it is disabled at that instant), to wait for the connection to be established (if it is not already connected). Then, further directives (see 2027) lead the user to place the chest piece on a first auscultation location on the torso of a subject (e.g. onto his/her chest wall), the position of which chest piece can preferably be depicted with a cursor or as a bounded region on a graphical representation appearing on a display screen 201 of the receiver unit 200. The application program 202 preferably waits for the user to press/switch/touch a Start button to start recording (see 2028), and then records auscultation sounds during a predefined time interval (see 2029). If the algorithm 2030 and FIG. 5 detects that the chest piece is not air-tight with subject's skin, or, that the subject does not inhale and/or exhale properly (e.g. that the subject holds breath or that the subject breathes with insufficient air volumes per inspiration and expiration), the application program 202 preferably warns the user accordingly and stops recording (see 2031), to wait for the next start-prompt. Upon successful completion of the recording (see 2032), several directives (see 2027) lead the user to continue with a subsequent predefined auscultation zone on the subject's torso, following a predefined sequence with regard to several predefined zones on said torso, until the recording with the last zone in the sequence is successfully completed (see 2033). Thus the user is instructed or guided for a sequential auscultation of several predefined zones on a subject's torso, which sequence is to be used in combination with different sound databases associated with each predefined zone for comparison. The user can listen (see 2034) to recorded sounds through a filter appropriately designed considering a normal user. The application program 202 may ask additional questions (see 2035) to the user (other than those asked for account creation), such as weight, length, smoking habits, current complaints etc. of a current subject; which questions may require text or numeric inputs and/or multiple choice answers. If a user chooses to continue (see 2036 and 2037), the application program makes the receiver unit send all data 2038 to the distant server 300 to be evaluated. The server 300 can verify the user type (see 301 in FIG. 6), performs computations and evaluations, and sends relevant outcomes (those that are limited suitably for the normal user) back to the receiver unit. The computations and evaluations performed in the server comprise flow signal estimation 302 from sound data, sub-phase division 303 such that the inspiration and expiration phases are divided into their early, mid and late portions (thus, six sub-phases in a full respiration cycle, three for inspiration and three for expiration), frequency domain transformations 304, calculation 305 of various spectral parameters and their comparison 306 with a healthy reference, crackle and wheeze detection 307, analysis 308 of detected crackles in terms of spectral and temporal characteristics such as their timing, class label (i.e. fine, medium, coarse), and count; analysis 309 of detected wheezes in terms of spectral and temporal characteristics such as their timing, at least one peak frequency component, and percentage of duration within flow sub-phase and/or cycle and/or total cycle; calculation of mathematical features through frequency representations, crackle-wheeze analyses, mathematical transforms, signal and system characterization methods, and parametric models (see 310); running learning (see 355 in FIG. 7) and classification (see 311) algorithms; decision fusion (see 312); and assessment of a probabilistic diagnosis of subject's condition (see 312). Graphical outputs that a normal user can be allowed to access include, but are not limited to:

(i) time plots of recorded sounds in association with predetermined auscultation zones on a subject's torso, where said user can select a plot window which is an amplitude-time window, a time interval or an amplitude interval to zoom in and zoom out, and can slide said plot window in any direction on the display, (ii) frequency (or time-frequency) plots of recorded sound data in association with pre-determined auscultation zones on a subject's torso, where all the zooming and sliding capabilities stated above in this paragraph are also valid for said frequency plots, (iii) visual/graphical representations based on spectral parameters, for comparing said representations of recorded sounds with suitable representations of healthy reference data in accordance with said zones and with each flow sub-phase (see 2200 in FIG. 12), (iv) a plurality of maps showing detected crackles with definitive color and/or shape-coded marks; a first one of said maps (see FIG. 8) showing on a time-frequency axis where time is expressed in terms of said six subsequent sub-phases of a flow cycle and frequency is expressed in terms of coarse/medium/fine crackle frequency bands, and a second one of said maps (see FIG. 10) showing on an image representing patient's torso with said zones, (v) another plurality of maps showing detected wheezes with color and/or shape and/or size-coded marks; a first one of said maps (see FIG. 9) showing on a time-frequency axis where time is expressed in terms of said six subsequent sub-phases of a flow cycle and frequency is represented in a continuous axis, a second one of said maps (see FIG. 10) showing on a chest-like image with said auscultation locations.

Thus, thanks to the abovementioned learning algorithms, the evolution of initially present databases on the system according to the present invention, related to various health conditions; and even creation of new databases related to diseases which are initially absent in database collections in said system, are enabled.

The system according to the present invention, in operation, displays said detected crackles with color codes and shape codes in a time-frequency representation (see FIG. 8), where time is expressed in said sub-phases of inspiration and expiration, and where frequency is expressed in terms of fine, medium and coarse crackle frequency ranges, and said detected wheezes with color codes and shape codes in a time-frequency representation (see FIG. 9), where time is expressed in said sub-phases of inspiration and expiration, and where frequency is a continuous axis.

A classification sequence is proposed according to the present invention, which sequence uses a sophisticated combination of algorithms for adventitious and vesicular sound classification, merging decisions specific for each respiration phase in a full respiration cycle (e.g. early, mid and late phases for both inspiration and expiration in a full respiration cycle). In a preferred embodiment of the system according to the present invention, a decision merging algorithm for different respiration phases is combined with Bayesian decision methods on a parametric or generative model in disease classification (e.g. GMM), and further combined with a linear discriminative classifier in multidimensional projection space for auscultation sounds classification (e.g. SVM).

Figure 10:
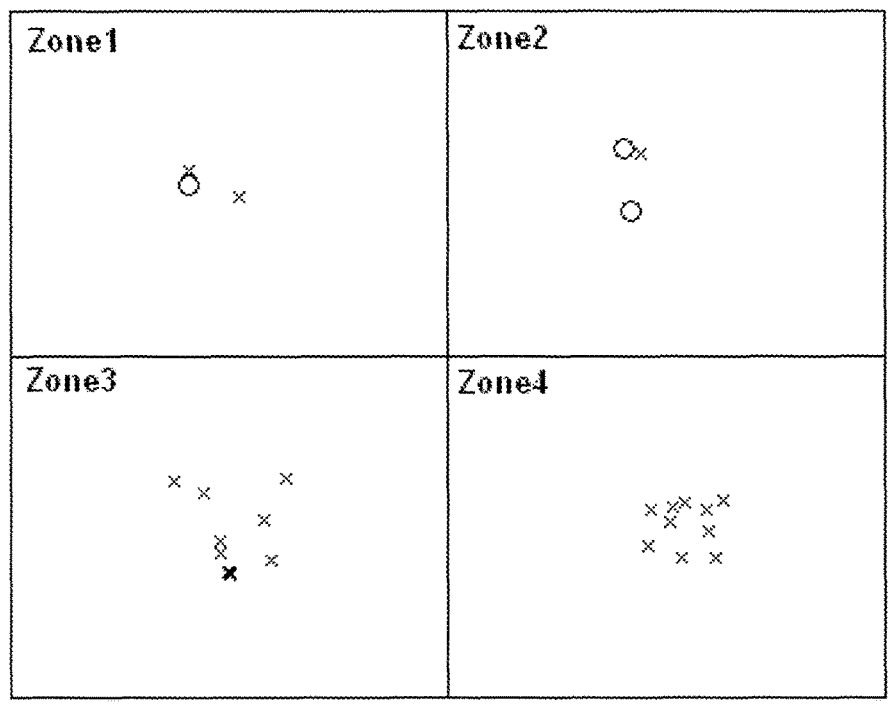
FIG. 10 shows representative illustrations for yet another type of graphical outputs provided by the system according to the present invention, for two different subjects, which displays the detected crackles and wheezes in color and shape codes with regard to the respective zones on the torso.
Figure 10:
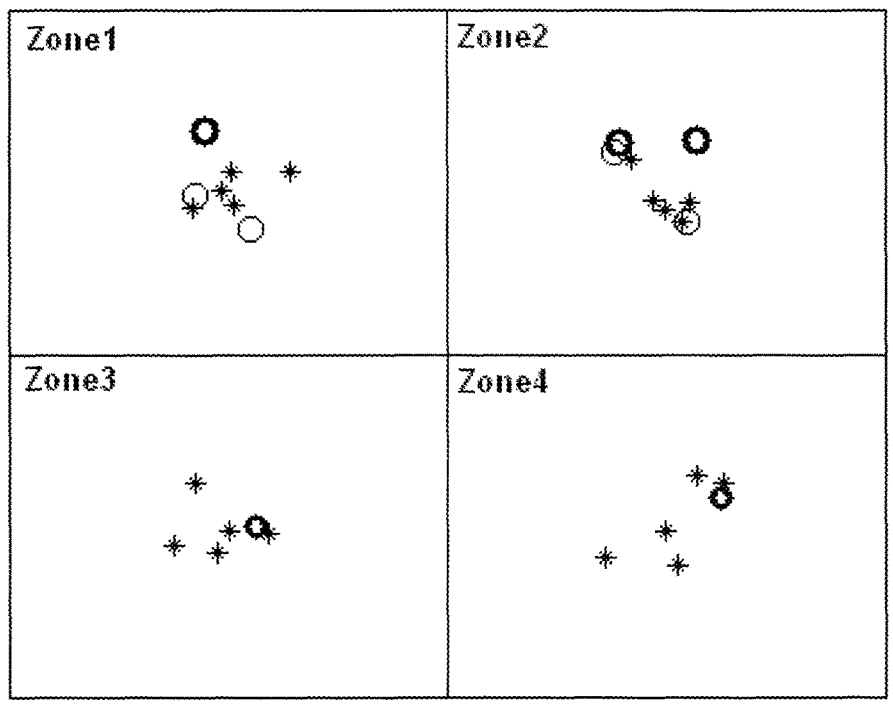
Figure 11:
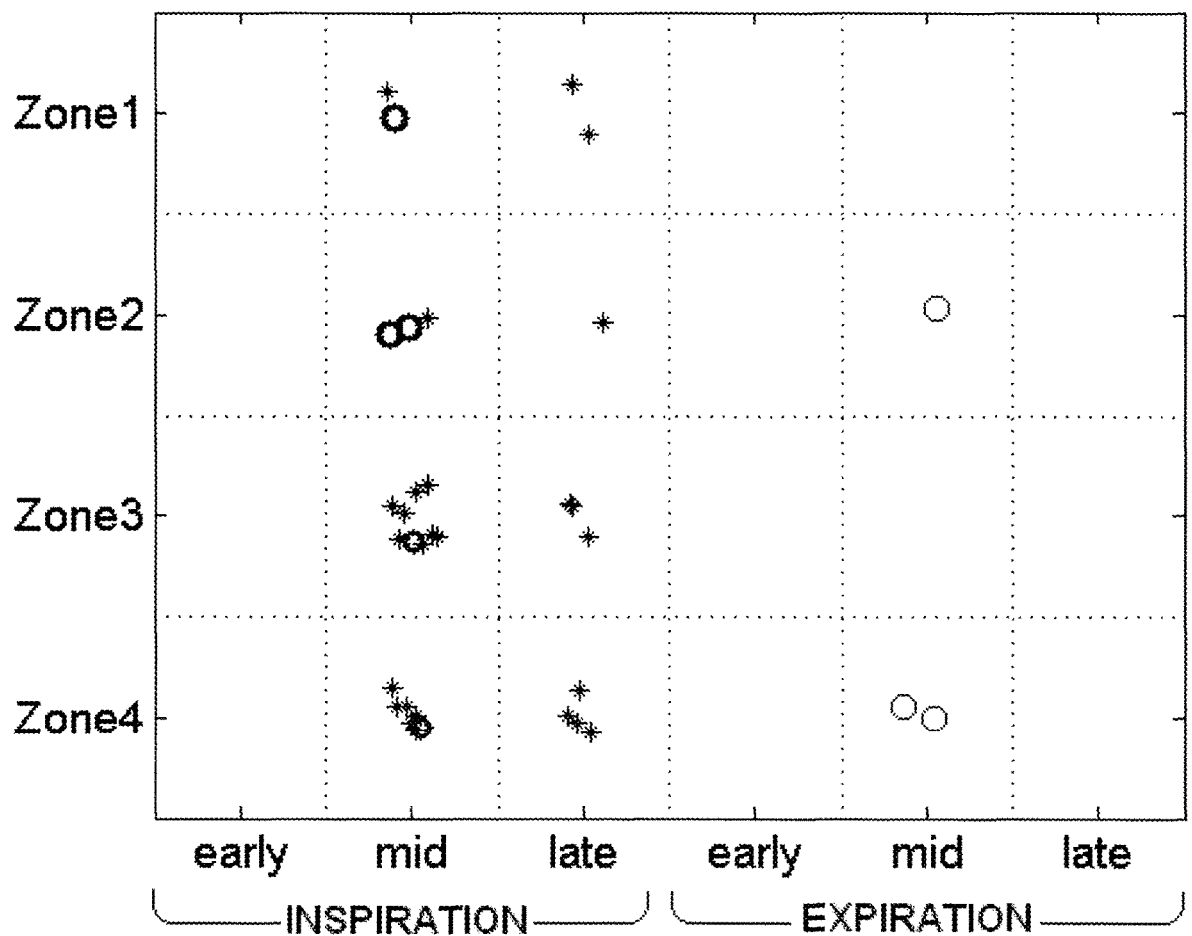
FIG. 11 shows a representative illustration for yet another type of graphical outputs provided by the system according to the present invention, which displays detected crackles and wheezes in color and shape codes with regard to the respective zones on the torso and also with regard to the respective sub-phases of flow cycle.

In a preferred embodiment according to the present invention, said system, in operation, maps said detected crackles and wheezes with regard to said zones, and displays said detected crackles and wheezes with color codes and shape codes (see FIG. 10 and FIG. 11).

Figure 4:
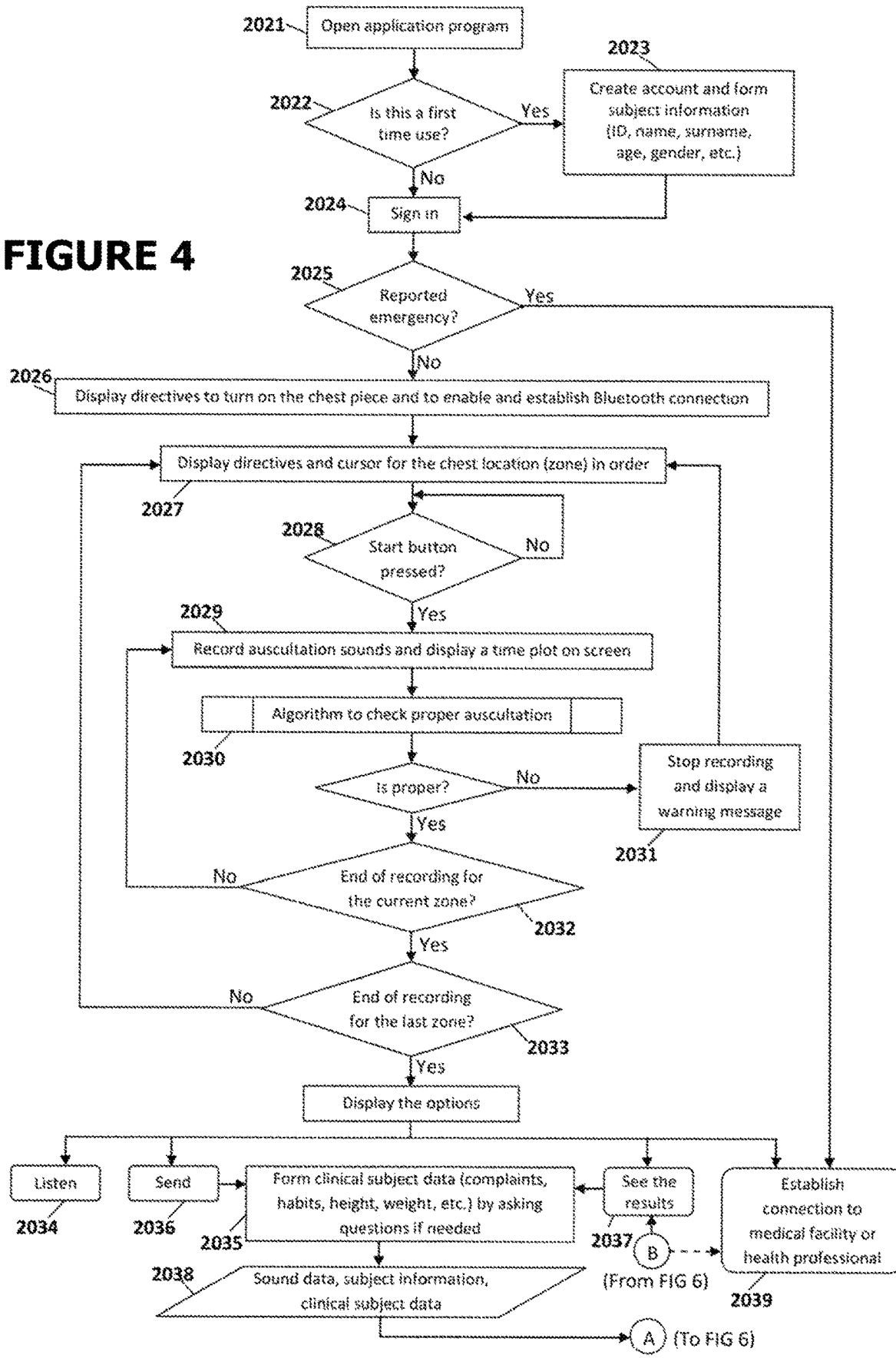
FIG. 4 shows a simplified flowchart illustrating the general operation of a suitable application program on the receiver unit forming part of the system of FIG. 1 according to the present invention.

Preferably, time-plots of recorded sounds are continuously updated and can be observed on a screen in real-time during recording (see 2029 in FIG. 4). Those time plots are to be updated (see 315 in FIG. 6) with special colored marks, letters and waveforms for estimated flow sub-phases and detected crackles and wheezes after this information is computed in the distant server and sent back to said receiver unit (see 2100 in FIG. 12). Preferable written and vocal reports that a normal user 10 can be allowed to access may include, but are not limited to:

(i) Written and vocalized versions of graphical outputs, (ii) A visual representation and written and vocal notifications of probabilistic diagnosis of subject's health condition which is sent as an output of classification algorithms that run on said distant server.

A user can access said outputs that he/she is authorized to access by pressing/touching/switching relevant buttons, or by activating associated tabs, and the like, in an application program 202 (in FIG. 2). All recorded data which are sent to said distant server, all outputs generated through computations and evaluations by distant server, and all other information associated with user are stored in the server, and are accessible by authorized components of the system according to the present invention, such as a main computer 400 (in FIG. 1) in a medical facility that can be assigned to said user regionally, or a health professional 11 that said user 10 is a regular patient of. Information can be appended in a line (see 351 in FIG. 7) to be accessed and examined by a personnel who is responsible for dealing with said records. In case of an emergency (e.g., due to results of an evaluation of recorded sound data) the distant server (which may be considered as central component of the system according to the present invention) produces an alert message in a suitable form, and delivers said message to relevant medical facility and/or professional responsible from the user, from starting a quickest communication form e.g. a text-to-speech message over a phone call. Alternatively, in case a user feels urgency (e.g., due to unbearable complaints), even by skipping sound recording (see 2025 in FIG. 4), he/she can communicate (see 2039 in FIG. 4) with a medical facility or professional through e-mail, SMS, call, or by any means that are technically possible at that moment. The communication can include sharing generated reports with a medical facility or professional using the system according to the present invention, the type of said reports depends on compatibility with a suitable communication form. Preferably, said application program 202 (in FIG. 1) on the receiver unit 200 (in FIG. 2) also keeps a summary information in said unit's memory, including selected parameters from each auscultation-evaluation session, to keep a track of any evolution of the health condition of a subject over time using any previously evaluated parameters associated with that subject. Preferably, a user can access tracking information at any time by entering said application program and can see it in a graphical form and/or as a short, written report.

After a health professional approves appended information (see 352 and 353 in FIG. 7), said information is preferably to be used in said server to update (see 355 in FIG. 7) learning algorithms. Updating the learning algorithms provides the objective technical effect of evolution of initially present databases related to various health conditions, and furthermore creation of new databases related to diseases which are initially absent in database. An application program 202 (in FIG. 2) running on said receiver unit 200 (in FIG. 1) can also receive any software updates sent through said distant server.

Typical operation of a preferred embodiment of the system according to the present invention by healthcare personnel is different from operation by a normal user in following aspects:
(i) A maximum number of allowed user accounts can be defined for a normal user, while it can be unlimited in healthcare personnel version of said application program,
(ii) said distant server identifies user type (see 301 in FIG. 7), and automatically (see 314 in FIG. 6) provides a greater variety of computations and evaluations to healthcare personnel in comparison with those provided to a normal user,
(iii) accordingly, graphical outputs and written reports are prepared in more detail and in a technical language, to which healthcare personnel are familiar, unlike individuals without medical training,
(iv) sounds recorded can be simultaneously shared with multiple other users to enable simultaneous listening and examination,
(v) filters for rendering said sound listenable with customary acoustic properties, can be selected among conventional bell and diaphragm modes or alternative suitable versions of convenience,
(vi) healthcare personnel can access any previous records, evaluation results, and all accompanying information of those normal users under his/her responsibility, and can enter commentary information into said system,
(vii) authorized healthcare personnel can access, examine and approve any appended information through said application program (as well as through computers in a medical facility using said system).

Thus, the system according to the present invention provides different levels of information obtained from auscultation data, levels of which are suitable and meaningful for either medical facilities, or healthcare personnel, or users without medical training.

The system according to the present invention records auscultation data in a broad frequency band such that any sound evaluation can be produced using calculations, and using said filters the system outputs a customary sound in a narrower frequency band for aural evaluation by health professionals. Thus said system uses and produces sound data both for computational and aural evaluation of auscultation data.

Typical operation of a preferred embodiment of a data acquisition (auscultation) device of a system according to the present invention would be generally the same in a general framework for the alternative embodiments of the device listed above, any differences being introduced due to appearance of said system but not its functionality.

The system according to the present invention is preferably modifiable and/or extendable, and/or expandable to record, send and process heart sounds in similar modes. Also other medical data such as blood pressure, $SpO_2$, blood sugar, ECG may be incorporated into the system.

The invention claimed is:
1. A process operating a data acquisition, communication and evaluation system, wherein the system comprises a chest piece for fitting to human skin, a receiver unit and a distant server, wherein
the chest piece encapsulates a sound transducer for acquiring raw sound data for being communicated in a form of a data signal,
the receiver unit is a portable device comprising a display unit and a data processing ability, wherein the receiver unit is in communication with the chest piece, and is further connectable to a local data network or global internet via a wired or wireless communication interface,
the distant server comprises computer coded instructions wherein the computer coded instructions process the data signals, stores medical information in association with the data signals and communicates the data signals and/or the medical information with at least two recipients, wherein the at least two recipients receive and send the data signals and/or the medical information, and wherein the at least two recipients are selected from a list consisting of devices held by a healthcare personnel, medical facilities and users, wherein the data signals and/or the medical information are selective based on the selected recipient,
the system further comprises a database, wherein the database is related with a different respective pre-determined zone on a human torso,
the system further comprises a plurality of pre-defined data acquisition channel and/or data acquisition location for evaluating data from the pre-determined zone, and
the system further comprises a computer-coded classifier, wherein the process comprises the following steps:
(a) the system generates directives for the user to place the chest piece at the pre-determined zones in accordance with a pre-determined sequence;
(b) the distant server of the system estimates an air flow signal from the data signal using mathematical algorithms, predicts inspiration and expiration phases comprising sub-phases, within a flow cycle, and predicts sub-phases of inspiration and sub-phases of expiration;
(c) the distant server of the system detects and computes (i) spectral and temporal characteristics of the crackles, comprising timing, a frequency content, and types in terms of fine, medium and coarse ranges, and counts, and (ii) spectral and temporal characteristics of the wheezes, comprising timing, at least one peak frequency component, and a percentage of duration within the sub-phases of inspiration and expiration, within inspiration and expiration, within the flow cycle, and over a total auscultation period;
(d) the distant server of the system generates and displays a frequency-domain representation with regard to the zone and the sub-phase, wherein the distant server of the system calculates and displays various parameters related to the auscultation and makes comparisons of the parameters against related parameters obtained from healthy reference data, and displays results of the comparisons;
(e) the distant server of the system displays (i) the detected crackles with color codes and shape codes in a time-frequency representation, wherein a time is expressed in the sub-phases of inspiration and expiration, and wherein a frequency is expressed in terms of the fine, medium and coarse crackle frequency ranges, and (ii) the detected wheezes with color codes and shape codes in the time-frequency representation, wherein the time is expressed in the sub-phases of inspiration and expiration, and wherein the frequency is a continuous axis;
(f) the computer-coded classifier utilizes information from the frequency-domain representations, and the time-frequency representations for the zone and sub-phase, together with mathematical transforms, signal and system characterization methods, and parametric models;

(g) the computer-coded classifier combines the data and calculations for the zone and sub-phase, and generates a probabilistic health condition report with regard to the database; and (h) the distant server of the system updates the computer-coded classifier as new data add to the database;

wherein time-plots of recorded sounds are continuously updated and observed on a screen in real-time during recording, and the time plots are updated with colored marks, letters and waveforms for estimated flow sub-phases and detected crackles and wheezes after the information is computed in the distant server and sent back to the receiver unit.

2. The process according to claim 1, wherein in the step (d) or (e), the distant server of the system displays a plot of the signal in a time domain with zooming and sliding capabilities, and the plot shows the sub-phases and adventitious sounds comprising the detected crackles and wheezes.

3. The process according to claim 1, wherein in the step (d) or (e), the distant server of the system maps the detected crackles and wheezes with regard to the zones and displays the detected crackles and wheezes with the color codes and shape codes.

4. The process according to claim 1, wherein information including data recorded from a subject and associated medical information which is selected from the list consisting of clinical subject data, algorithmic evaluation and outcomes from the system, and medical evaluation information given by the healthcare personnel, are selectively accessible for the users, such that respective data can be accessed by non-health-professional users, and health professionals.

5. The process according to claim 1, wherein before the step (b), the distant server of the system checks for the auscultation by (i) checking whether the chest piece is placed correctly, and (ii) checking whether the subject inspires and expires properly such that sufficient air volumes for collecting the data is inhaled and exhaled.

6. The process according to claim 1, wherein before the step (b), the chest piece of the system filters the data signals according to a pre-defined frequency response shape including a conventional bell and diaphragm modes.

7. The process according to claim 4, wherein the distant server of the system tracks in time the probabilistic health condition and reports any changes in the probabilistic health condition or the parameters selectively for the users, and gives the respective data to the health professionals, the healthcare personnel and non-healthcare personnel users.

* * * * *